United States Patent [19]
Kirschner et al.

[11] Patent Number: 5,886,048
[45] Date of Patent: Mar. 23, 1999

[54] PHMB FOR THE TREATMENT OF TUMOR DISEASE

[75] Inventors: Ulrich Kirschner; Frank Jethon, both of Bad Homburg, Germany

[73] Assignee: Fresenius AG, Germany

[21] Appl. No.: 893,301

[22] Filed: Jul. 15, 1997

[30] Foreign Application Priority Data

Jul. 16, 1996 [DE] Germany .................. 196 28 641.7

[51] Int. Cl.⁶ .................................................. A61K 31/155
[52] U.S. Cl. .............................................................. 514/635
[58] Field of Search ............................................. 514/635

[56] References Cited

FOREIGN PATENT DOCUMENTS 0 450 117 A1  10/1991  European Pat. Off. .
19628641 A1   1/1998  Germany ................................ 514/635

*Primary Examiner*—Jerome D. Goldberg
*Attorney, Agent, or Firm*—Kenyon & Kenyon

[57] ABSTRACT

Use of poly(hexamethylene) biguanide (PHMB) for the treatment of tumor disease or tumors, such as, e.g., colon tumors, melanomas, kidney tumors, ovarian tumors, lung tumors, breast tumors, pancreas tumors, and the like is disclosed. Use is especially focused on the treatment of colon tumors, lung tumors, melanomas, kidney tumors and breast tumors. PHMB with a mean molecular-weight distribution of up to 15,000 is suitably used.

15 Claims, 2 Drawing Sheets

PHMB FOR THE TREATMENT OF TUMOR DISEASE

FIELD OF THE INVENTION

The subject of the present invention is the use of poly (hexamethylene) biguanide for the treatment of tumor disease.

BACKGROUND OF THE INVENTION

From the state of the art we know that poly (hexamethylene) biguanide (PHMB) has a bactericidal and fungicidal action (cf., e.g., British Patent 1,202,495). PHMB is therefore applied in many areas as a disinfecting agent, e.g., in the form of solutions or sprays. Applications are found in, e.g., the food industry to clean and disinfect spaces and instruments, to stabilize beverages as well as clean and stabilize water, e.g., also in swimming pools to combat the proliferation of algae and bacteria. From German Published Unexamined Application DE-OS 35 37 627 it is known that, by combining PHMB having a molecular weight ranging from 1,700 to 2,500 with a small amount of polyethyelene glycol, disinfecting agents are obtained that are also used as local antiseptics in the treatment of wounds. According to this German Published Unexamined Application, the PHMB that is marketed by ICI as the hydrochloride under the trademark Vantocil® is a suitable PHMB.

European Patent 0 4 50 117 describes a Ringer's solution and its use as a bactericidal local wound-treatment medication in which the lactate-free Ringer's solution contains in addition 0.1% to 0.2% of a dissolved concentrate that consists of a 20% aqueous poly(hexamethylene) biguanide hydrochloride solution in which 1 g per 100 ml of polyethylene glycol with a molecular weight of approximately 4,000 is dissolved. Also described as a suitable PHMB is the product marketed by the ICI company under the trademark Vantocil® IB. A product under the trademark Lavasept® is known for healing wounds, the Lavasept concentrate being an aqueous solution of 20 percent by weight of PHMB and 1 percent by weight of polyethylene glycol 4,000, and the PHMB being the commercial product Vantocil® IB of the ICI company.

U.S. Pat. No. 4,758,591 describes solutions containing a microbicidal or fungicidal amount of a biguanide or of a water-soluble salt thereof in the amount of 0.000001 to 0.0003 percent by weight which is used for contact lenses, ophthalmologic products, and dermatological formulations in the vicinity of the eye.

British Patent 1,432,345 discloses combinations for use in connection with the eyes and contact lenses which contain at least one ophthalmologically acceptable polymeric biguanide.

Tumors continue to rank among the most frequent diseases, and numerous agents have been proposed and used for their treatment with varying results.

The synthesis and development of novel antitumoral substances as well as the screening among known substances for those that possess antitumoral properties have been a major concern of today's cancer research.

There continues to be a need for suitable agents for effectively treating tumors or tumor diseases.

OBJECTS AND SUMMARY OF THE INVENTION

The object of the present invention is therefore to make available an agent for treating tumor diseases more effectively and more rapidly. Specifically, the goal is to make available an agent that can be used locally and, if applicable, systemically and that is highly effective against tumors without destroying the cells of the surrounding tissue.

According to the invention, it was surprisingly found that this problem can be solved by the use of poly (hexamethylene) biguanide (PHMB). PHMB can inhibit the growth of various kinds of tumors. It was further surprisingly found according to the invention that poly (hexamethylene) biguanide has a selective effect on specific types of tumors, in particular carcinomas of the colon. Among the kinds of tumors sensitive to PHMB are those which are highly resistant to other known antitumoral agents (cf., e.g., *Eur J Cancer Clin Oncol* 1987, 123:937–948; Fiebig, Berger (eds.) Immunodeficient Mice in *Oncology, Contrib. Oncol* Basel, Karger, 1992, Vol. 42, 321–351: *Med Welt* 1984, 35:52–58, 81–86).

Preferred, according to the invention, is a poly (hexamethylene) biguanide with a mean molecular weight distribution of up to 15,000.

Especially preferred is a poly(hexamethylene) biguanide with a mean molecular weight distribution of 1,000 to 8,000 and, in particular, a PHMB with a mean molecular weight distribution of 1,700 to 5,000, e.g., with a mean molecular weight (MW) of 2,600, of 2,800, of 3,500, of 4,000 or of 4,500. Molecular weight determination is carried out viscosimetrically.

DETAILED DESCRIPTION OF THE PREFERRED EMBODIMENTS

Figure 1:
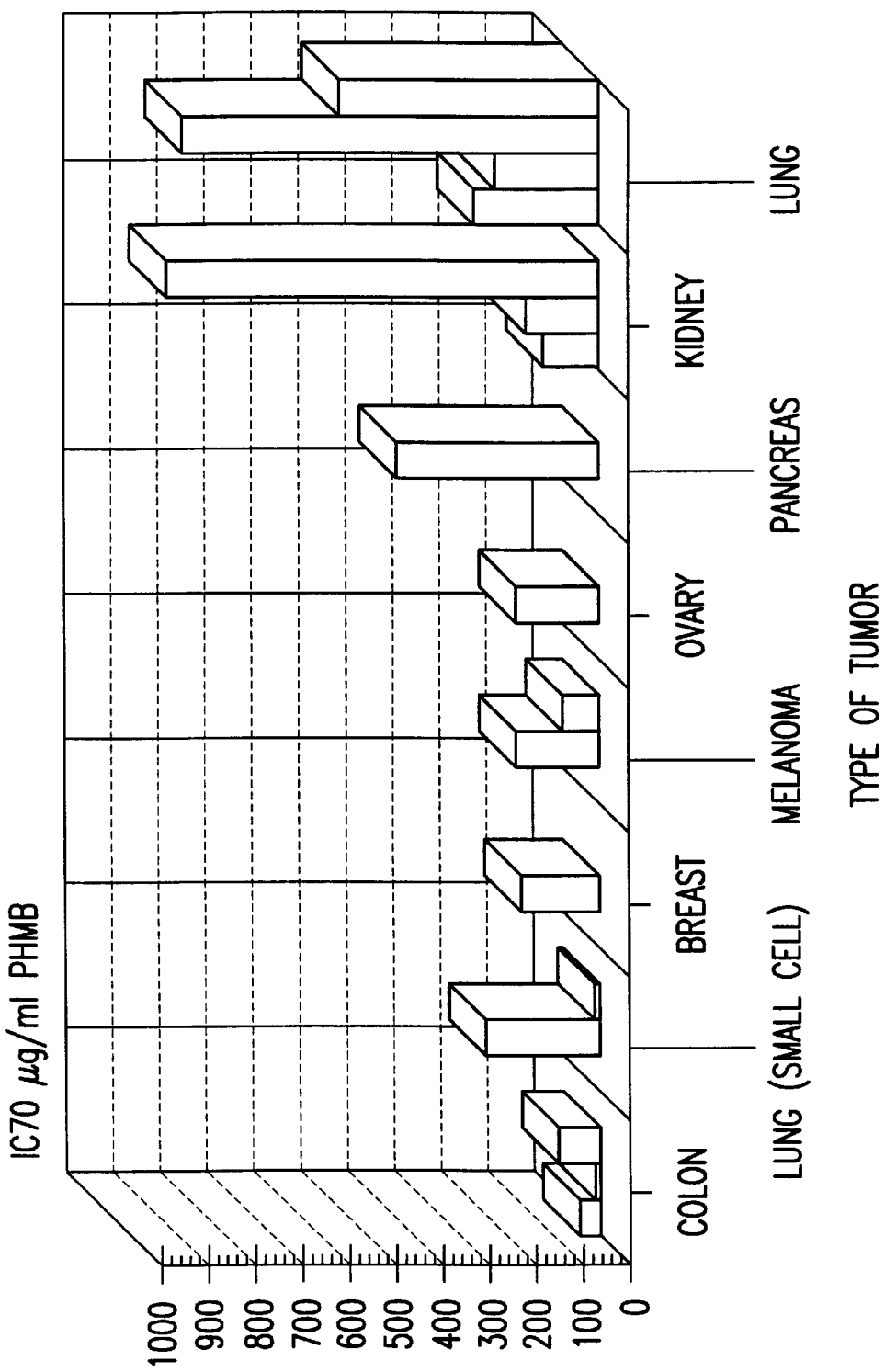
FIG. 1 is a chart demonstrating the effect of PHMB on the growth of various types of tumors, according to the invention.

The poly(hexamethylene) biguanide according to the invention is prepared in otherwise known manner, e.g., as described in German Patent 16 20 938 or British Patent 1,202,495, the disclosure of which are incorporated herein by reference. From the poly(hexamethylene) biguanide obtained an undesirable molecular weight portion can, if applicable, be separated in otherwise known manner, e.g., by dialysis, molecular filtration, HPLC, gel permeation chromatography (GPC), fractional precipitation, and the like. For example, the low-molecular constituents can be removed in this manner from the commercially available PHMB to obtain a PHMB of low toxicity yet equal effectiveness. In this connection, the disclosure of PCT/EP94/01587 is incorporated herein by reference.

Suitable according to the invention are such commercially available PHMBs as, e.g., Vantocil® IB, Cosmocil CQ, or Arlagard® E or other commercial products, from which the undesirable toxic low-molecular fraction has been separated, if applicable, as described above.

The PHMB used according to the invention is present in free form or in the form of a salt, such as a water-soluble salt, e.g., a hydrochloride, as a powder (e.g., freeze-dried) in 100% concentration or in aqueous solution. It is available in the aqueous solution (i.e., as concentrate) in a concentration of up to 40 percent by weight, e.g., in 2 to 40 percent by weight, preferably 3 to 30 percent by weight, especially 4 to 20 percent by weight, e.g., 4 percent by weight, 4.5 percent by weight, 5 percent by weight, or 6 percent by weight.

The term "PHMB" is understood to refer herein to poly(hexamethylene) biguanide as well as to poly(hexamethylene) biguanide in the form of a salt, e.g., a water-soluble salt, such as the hydrochloride.

The concentration in which the PHMB or the aqueous solution of PHMB is used according to the invention for the treatment of tumors or tumor disease depends on the purpose for which its use is intended. Suitable concentrations generally lie in the range of 0.0001 to 1 percent by weight, preferably in the range of 0.0005 to 0.1 percent by weight, especially in the range of 0.001 to 0.04 percent by weight, for example, 0.01 or 0.03 percent by weight (in terms of the PHMB).

The PHMB used according to the invention can be combined with surface-tension-lowering surfactants, e.g., polyethylene glycol. Preferably polyethyelene glycol with a molecular weight of 1,500 to 6,000 is used, and in particular polyethylene glycol with a molecular weight of 4,000, such as is marketed by the BASF AG company under the trademark Lutrol® E 4000. The proportion of PHMB to the surfactant lies suitably in the range of 6:1 to 24:1, preferably in the range of 12:1 to 22:1 and, in particular, is 20:1.

The PHMB used in accordance with the invention is highly effective against tumors, such as, e.g., colon tumors, melanomas, kidney tumors, ovarian tumors, lung tumors, breast tumors, pancreas tumors, and the like. It is used especially for the treatment of colon tumors, lung tumors, melanomas, kidney tumors and breast tumors. In accordance with the invention, it is used in particular for the treatment of tumors of the colon.

Treatment according to the invention is local or systemic, e.g., oral, rectal, vaginal or parenteral, preferably, however, local.

Depending on the planned treatment, application can be, e.g., in the form of drops, aqueous solutions (containing, if applicable, lactate-free Ringer's solution or sodium chloride solution, preferably lactate-free Ringer's solution), emulsions, suspensions, gels, ointments, pastes, creams, coated tablets or plain tablets. Special examples are solutions for intratumoral injections, e.g., in forms of skin cancer, such as melanomas;

gels, ointments, pastes for external application, e.g., in forms of skin cancer, such as melanomas;

solutions for intraperitoneal irrigations, e.g., in forms of carcinoma metastasizing into the peritoneal cavity (e.g., colon carcinomas);

solutions for colonic irrigations;

solutions for urethral irrigations;

dosage forms resistant to gastric juice, such as, e.g., coated tablets which allow the active substance to be released selectively, e.g., in the intestinal tract;

dosage forms which allow the active substance to be released selectively, e.g., in the stomach;

i.v. solutions, with a PHMB fraction especially prepared for such administration (i.e., PHMB from which the portions of low molecular weight have been removed, e.g., PHMB with a mean molecular weight of 2,900 to 15,000, as described in the PCT/EP94/01587).

Additionally contained in these formulations are, if applicable, the adjuvants and additives necessary for the preparation of the respective formulation.

The product can be used in humans and other animals, preferably in humans.

The examples which follow serve to illustrate the present invention.

EXAMPLE 1

From poly(hexamethylene) biguanide hydrochloride with a mean molecular weight (MW) of 2,800, polyethylene glycol 4,000 (Lutrol® E 4000, BASF AG), and water a solution of the following composition was prepared by mixing:

| | |
|---|---|
| poly(hexamethylene) biguanide hydrochloride, MW of 2,800 | 20 percent by weight |
| polyethylene glycol, MW of 4,000 | 1 percent by weight |
| water | 79 percent by weight |

After suitable dilution, the prepared solution was successfully used for the treatment of tumors.

The commercially available poly(hexamethylene) biguanide product Vantocil® IB, Cosmocil CQ, or Arlagard® E of the ICI company was used as the poly(hexamethylene) biguanide hydrochloride. Vantocil® IB, Cosmocil CQ, or Arlagard® E are aqueous solutions which contain 20% poly(hexamethylene) biguanide hydrochloride as active substance.

EXAMPLE 2

Example 1 was repeated for the preparation of another solution for use according to the invention, with the exception that instead of PHMB hydrochloride the corresponding PHMB was used.

EXAMPLE 3

Testing of the antitumoral effectiveness of PHMB hydrochloride having a MW of 2,800.

The testing was carried out using the solution according to Example 1 in the following manner:

The testing was carried out in the types of tumors listed in Table 1, the properties of which have been characterized in the literature (e.g., Berger et al.: "Establishment and Characterization of Human Tumor Xenografts in Thymus-Aplastic Nude Mice," in: Fiebig, Berger (eds.) *Immunodeficient Mice in Oncology*. Contrib. Oncol., Basel, Karger, 1992; Fiebig, Berger (eds.), *Immunodeficient Mice in Oncology*. Contrib. Oncol., Basel, Karger, 1992, Vol. 42, p. 97–97, and Fiebig, Berger (eds.) *Immunodeficient Mice in Oncology*. Contrib. Oncol., Basel, Karger, 1992, Vol. 42, pp. 148–151).

TABLE 1

| "Tumor types" | |
|---|---|
| Name | Origin |
| CFX 280 | colon |
| CXF 609 | colon |
| CXF HT29X | colon |
| LXFA 289 | lung |
| LXFA 526 | lung |
| LXFE 409 | lung |
| LXFL 529 | lung |
| LXFS 538 | lung (small-cell) |
| LXFS 650 | lung (small-cell) |
| MAXF MCF7X | breast |
| MEFX 514 | melanoma |
| MEFX 989 | melanoma |
| OVXF 1023 | ovary |
| PRXF PC3M | pancreas |

TABLE 1-continued

"Tumor types"

| Name | Origin |
|---|---|
| RXF 486 | kidney |
| RXF 1220 | kidney |
| RXF 944LX | kidney |

The in vitro activity of PHMB against the stem-cell fraction of the particular tumor type was tested according to a modified two-layer soft agar culture system protocol of Fiebig et al. (Eur J Cancer Clin Oncol 1987, 123:937–948; Fiebig, Berger (eds.) *Immunodeficient Mice in Oncology.* Contrib. Oncol., Basel, Karger, 1992, Vol. 42, pp. 321–351: *Med Welt* 1984; 35:52–58, 81–86), according to Hamburger and Salmon (*Science* 197:461–463, 1977). The individual testing steps are described below:

Solid tumor material was carefully mechanically disintegrated into small-cut pieces in a "stomacher" and incubated for 30 minutes at 37° C. with an enzyme cocktail of 0.05% collagenase, 0.07% DNAse, and 0.1% hyaluronidase. The cells were then washed twice with cell-culture medium and passed in succession through screens with mesh sizes of 200 $\mu$m and 50 $\mu$m. The proportion of available cells was determined in a hemocytometer by the trypan blue exclusion method (intact cells remained unstained by the dye).

The tumor-cell suspension was poured into multititration plates with 24 wells over a bottom layer containing 0.2 ml Iscoves culture medium with 20% fetal calf serum and 0.7% agar. Added were 20,000 to 200,000 cells to 0.2 ml of the same cell culture medium with 0.4% agar, and the suspension poured onto the bottom layer plates. Because of the small proportion of agar, the medium assumes a sponge-like structure, making possible a three-dimensional growth of the tumor colonies. The various concentrations of the test substance were tested in triple determinations with continuous exposure (drug overlay method) in 0.2 ml of cell culture medium against a control without test substance. The cultures were incubated for 6–18 days at 37° C. and 7% $CO_2$ in an atmosphere saturated with atmospheric humidity.

Colony growth was determined in the control batches without active substance using an inverted microscope. During the incubation colonies with a diameter >50 $\mu$m form as a result of in vitro growth. The multititration plates were evaluated during the greatest colony growth by means of an automatic image-analyzing system (Bausch and Lomb, Omnicom FAS IV). To obtain better contrast the colonies were stained with tetrazolium chloride 24 hours before the evaluation.

Treatment of the Test Cultures with the Test Substance

Various concentrations of the PHMB hydrochloride (MW of 2,800) were tested in gradations of 10, 30, 100, 300, and 1000 $\mu$g/ml. Depending on the proliferation time, the incubation period was 5 to 18 days. A threefold concentration of the test substance was diluted with nutrient medium and poured as top layer into the wells of the microtitration plates. This established the desired final concentration of the test substance in the bottom layer and the tumor cell layer through diffusion.

Control batches without test substance were simultaneously run in each experiment to determine growth. Batches with reference substance 5-FU were simultaneously included as positive controls.

To calculate the effectiveness of the test substance, the number of surviving cell colonies of the various types of tumors was determined in terms of percent by relating the number of colonies in the treated test batches (T=test) with the number of colonies in the control batches (C=control) in the following proportion:

$$T/C = \text{number of colonies}_{untreated\ control} \times 100 / \text{number of colonies}_{control\ batch}$$

A test was rated as fully evaluable when the following quality criteria were met:

a) number of colonies in the control batches with a diameter of 50 $\mu$m>20;

b) starting number of colonies on Day 0 or 2<30% of the final number of colonies in the control;

c) coefficient of variation in the control group <50%;

d) survival rate with the reference substance 5-FU at the toxic dose of 1000 $\mu$g/ml<30% of the untreated control batch.

The following results were obtained in this testing:

At a concentration of 300 $\mu$g/ml, the PHMB inhibited the colony growth to less than 30% of the control (=effective) in 13 of 17 tested types of tumors. At a concentration of 100 $\mu$g/ml, 5 of the tumor types tested were still inhibited to 30% of the control growth. The results are listed in Table 2 and graphically illustrated in FIG. 1.

The concentrations at which tumor growth was inhibited to 30% of the control growth are indicated in $IC_{70}$ values (concentration, in $\mu$g/ml, at which 70% of the colonies were killed).

The most sensitive tumors were the colon carcinomas CXF 280, CXF 609 and HT29X, the (small-cell) lung carcinoma LXFS 650, the melanoma MEFX 989, the kidney carcinomas RXF 486 and RXF 1220, and the breast carcinoma MCF7.

TABLE 2

Action of poly(hexamethylene) biguanide (PHMB) on the growth of various types of tumor in terms of the $IC_{70}$ values.

| Cell line | Type of tumor | $IC_{70}$ $\mu$g/ml PHMB T/C < 30% |
|---|---|---|
| CFX 280 | colon | 41.485 |
| CFX 609 | colon | 13.687 |
| CXF HT29X | colon | 85.658 |
| LXFA 289 | lung | 283.145 |
| LXFA 526 | lung | 186.366 |
| LXFE 409 | lung | 897.583 |
| LXFL 529 | lung | 468.224 |
| LXFS 538 | lung (small-cell) | 256.425 |
| LXFS 650 | lung (small-cell) | <10 |
| MAXF MCF7X | breast | 175.332 |
| MEFX 514 | melanoma | 182.074 |
| MEFX 989 | melanoma | 87.671 |
| OVXF 1023 | ovary | 186.070 |
| PRXF PC3M | pancreas | 529.431 |
| RXF 486 | kidney | 115.407 |
| RXF 1220 | kidney | 175.009 |
| RXF 944LX | kidney | 922.439 |

The colon carcinomas CXF 280 and CXF 609 and the lung carcinoma LXFS 650 showed a special sensitivity to PHMB which was greater by one log level than the other sensitive tumor types. The third colon tumor CXF HT29X was also among the most sensitive tumors.

EXAMPLE 4

Testing of the antitumoral effectiveness of PHMB with a MW of 2,800.

The testing was carried out using the solution prepared according to Example 2 in the manner described in Example 3.

The results obtained in this testing were comparable to those described under Example 3.

EXAMPLE 5

Example 1 was repeated in preparing another solution according to the invention, except that water was used instead of polyethylene glycol of MW 4,000. The solution obtained had the following composition:

| | |
|---|---|
| PHMB hydrochloride with a MW of 2,800 | 20 percent by weight |
| Water | 80 percent by weight. |

This solution was tested in the same manner as in Example 3, the results obtained being comparable to those described under Example 3.

EXAMPLE 6

Example 5 was repeated for the preparation of a solution according to the invention, except that the corresponding PHMB was used instead of PHMB hydrochloride.

EXAMPLE 7

Using PHMB with a molecular weight of 3,500, polyethylene glycol 4,000, and water, a solution of the following composition was prepared in the same manner as described in Example 1 by mixing the constituents:

| | |
|---|---|
| poly(hexamethylene) biguanide hydrochloride, MW of 3,500 | 20 percent by weight |
| polyethylene glycol, MW of 4,000 | 1 percent by weight |
| water | 79 percent by weight |

The poly(hexamethylene) biguanide hydrochloride used was separated in otherwise known manner by fractional distillation from the commercially available poly(hexamethylene) biguanide product Vantocil® IB, Cosmocil CQ or Arlagard E of the ICI company. Vantocil® IB, Cosmocil CQ or Arlagard E are aqueous solutions containing 20% poly(hexamethylene) biguanide hydrochloride as the active substance.

EXAMPLE 8

Example 7 was repeated for the preparation of another solution according to the invention, except that PHMB hydrochloride with a MW of 5,000 prepared in the same manner was used instead of the PHMB hydrochloride with a MW of 3,500 used there.

EXAMPLE 9

A solution according to the invention of the following composition was prepared by mixing PHMB with a mean molecular weight of 4,000 and water:

| | |
|---|---|
| PHMB, MW of 4,000 | 4.5 percent by weight |
| water | 95.5 percent by weight. |

The PHMB used was obtained in the manner described in Example 7.

Figure 2:
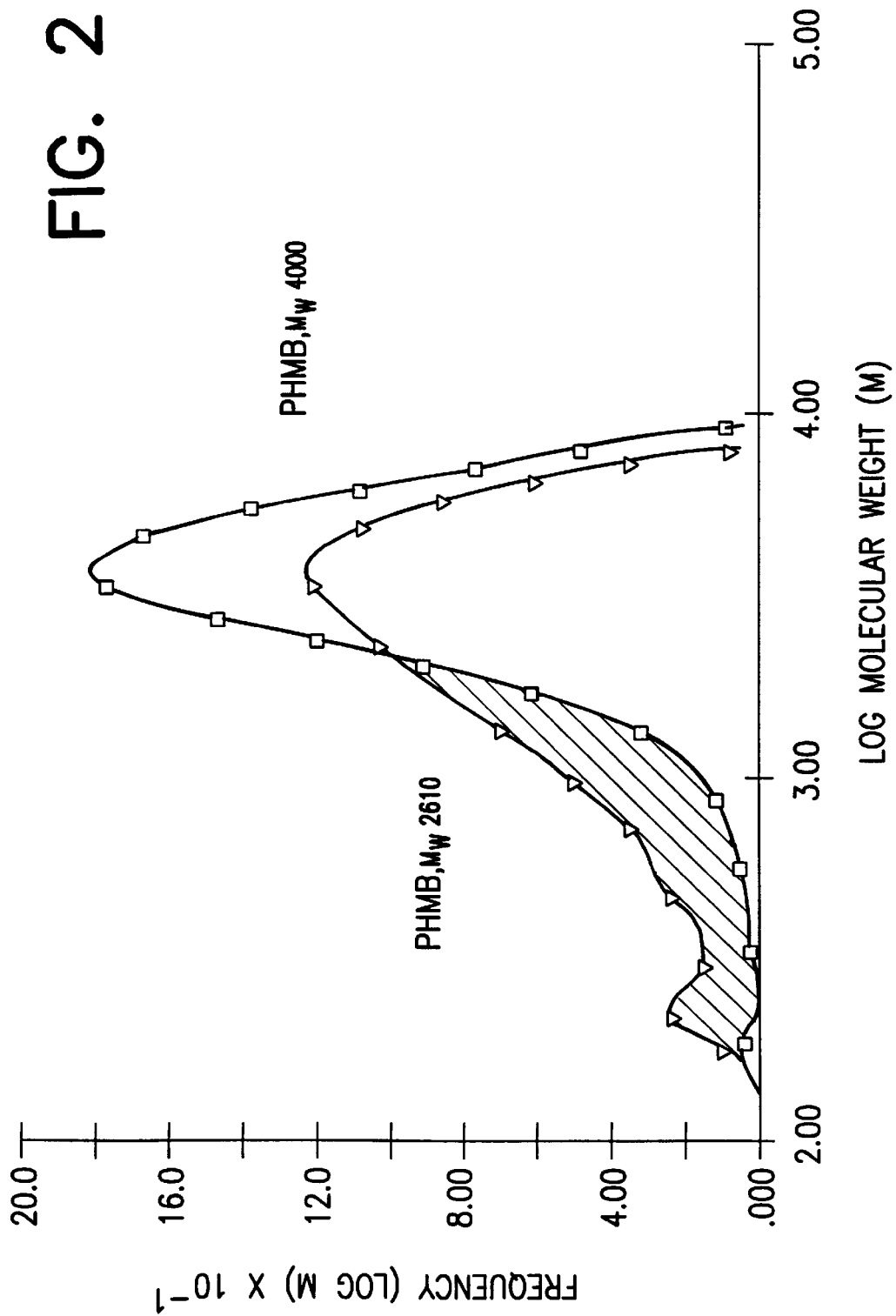
FIG. 2 is a graph showing molecular-weight distribution of PHMB with a MW of 2610 and PHMB with a MW of 4000.

FIG. 2 shows the molecular weight distribution of PHMB with a MW of 4,000 compared to commercially available PHMB with a MW of 2,600.

EXAMPLE 10

A solution according to the invention of the following composition was prepared by mixing PHMB with a mean molecular weight of 5,000 and water:

| | |
|---|---|
| PHMB, MW of 5,000 | 4.0 percent by weight |
| water | 96.0 percent by weight. |

The PHMB used was obtained in the manner described in Example 7.

EXAMPLE 11

A solution according to the invention of the following composition was prepared by mixing PHMB with a mean molecular weight of 4,500 and water:

| | |
|---|---|
| PHMB, MW of 4,500 | 4.2 percent by weight |
| water | 95.8 percent by weight. |

The PHMB used was obtained in the manner described in Example 7.

EXAMPLE 12

A solution according to the invention of the following composition was prepared by mixing PHMB with a mean molecular weight of 4,000 and water:

| | |
|---|---|
| PHMB, MW of 4,000 | 20 percent by weight |
| water | 80 percent by weight. |

The PHMB used was obtained in the manner described in Example 7.

EXAMPLE 13

For the preparation of a solution for intravenous administration, the solution prepared in Example 11 was diluted with lactate-free Ringer's solution to a final PHMB concentration of 0.0012 percent by weight with a MW of 4,500.

EXAMPLE 14

For the preparation of another solution for intravenous administration, the solution prepared in Example 11 was diluted with lactate-free Ringer's solution to a final PHMB concentration of 0.01 percent by weight with a MW of 4,500.

EXAMPLE 15

For the preparation of another solution for intravenous administration according to the invention, the solution prepared in Example 10 was diluted with 0.9% sodium chloride solution to a final PHMB concentration of 0.005 percent by weight with a MW of 5,000.

We claim:

1. A method of treating tumor disease sensitive to the compound below, comprising administering to a human having a tumor disease a therapeutically effective amount of poly(hexamethylene) biguanide or a salt thereof.

2. A method according to claim 1, wherein the poly (hexamethylene) biguanide has a mean molecular weight distribution of up to 15,000.

3. A method according to claim 2, wherein the poly (hexamethylene) biguanide has a mean molecular weight distribution of between 1,000 and 8,000.

4. A method according to claim 3, wherein the poly (hexamethylene) biguanide has a mean molecular weight distribution of between 1,700 and 5,000.

5. A method according to any of claim 2, wherein the poly(hexamethylene) biguanide is administered in a composition further comprising a surface-tension-lowering surfactant.

6. A method according to claim 5, wherein the surfactant is polyethylene glycol.

7. A method according to claim 6, wherein the ratio of poly(hexamethylene) biguanide to polyethylene glycol in the composition is in the range of 6:1 to 24:1.

8. A method according to claim 7, wherein the ratio is in the range of 12:1 to 22:1.

9. A method according to claim 6, wherein the poly (hexamethylene) biguanide is administered in a solution selected from the group consisting of lactate-free Ringer's solution or sodium chloride solution.

10. A method according to claim 9, wherein the poly (hexamethylene) biguanide is administered in a concentration of 0.0001 to 0.1 percent by weight.

11. A method according to claim 10, wherein the poly (hexamethylene) biguanide is administered in a concentration of 0.0005 to 0.05 percent by weight.

12. A method according to claim 11, wherein the poly (hexamethylene) biguanide is administered in a concentration of 0.001 to 0.04 percent by weight.

13. A method for treating tumor disease sensitive to the compound below, comprising administering to an animal having a tumor disease a therapeutically effective amount of poly(hexamethylene) biguanide or a salt thereof.

14. A method according to claim 13, wherein the poly (hexamethylene) biguanide has a mean molecular weight distribution of between 1,700 and 5,000.

15. A method according to claim 14, wherein the poly (hexamethylene) biguanide is administered in a composition further comprising polyethylene glycol, at a ratio of poly (hexamethylene) biguanide to polyethylene glycol of between 12:1 and 22:1.

* * * * *